US005807537A

United States Patent [19]

Dean et al.

[11] Patent Number: 5,807,537
[45] Date of Patent: *Sep. 15, 1998

[54] TECHNETIUM-99M LABELED PEPTIDES FOR IMAGING COMPRISING A SINGLE THIOL MOIETY

[75] Inventors: Richard T. Dean, Bedford; William McBride, Manchester; Scott Buttram, Derry, all of N.H.

[73] Assignee: Diatide, Inc., Londonderry, N.H.

[*] Notice: The term of this patent shall not extend beyond the expiration date of Pat. No. 5,443,815.

[21] Appl. No.: 462,212

[22] Filed: Jun. 5, 1995

Related U.S. Application Data

[62] Division of Ser. No. 807,062, Nov. 27, 1991, Pat. No. 5,443,815.

[51] Int. Cl.⁶ .......................... A61K 51/00; A61M 36/14
[52] U.S. Cl. .......................... 424/1.69; 530/300; 534/14
[58] Field of Search ........................ 424/1.69; 530/300, 530/324, 325, 326, 327, 328, 329, 330; 534/10–16

[56] References Cited

U.S. PATENT DOCUMENTS

| | | | |
|---|---|---|---|
| 4,311,639 | 1/1982 | Ganfield et al. | 260/112.5 |
| 4,434,151 | 2/1984 | Byrne et al. | |
| 4,444,690 | 4/1984 | Fritzberg . | |
| 4,472,509 | 9/1984 | Gansow et al. | |
| 4,493,795 | 1/1985 | Nestor, Jr. et al. | 260/112.5 |
| 4,571,430 | 2/1986 | Byrne et al. | |
| 4,575,559 | 3/1986 | Byrne et al. | |
| 4,611,054 | 9/1986 | Fritzberg . | |
| 4,859,765 | 8/1989 | Nestor, Jr. et al. | 530/333 |
| 4,861,869 | 8/1989 | Nicolotti et al. | |
| 4,986,979 | 1/1991 | Morgan, Jr. et al. | 424/1.11 |
| 4,988,496 | 1/1991 | Srinivason et al. | 424/1.11 |
| 5,061,641 | 10/1991 | Schochat et al. | |
| 5,094,848 | 3/1992 | Brixner et al. | 424/1.11 |
| 5,196,510 | 3/1993 | Rodwell et al. | |
| 5,225,180 | 7/1993 | Dean et al. | 424/1.69 |
| 5,248,764 | 9/1993 | Flanagan et al. | |
| 5,405,597 | 4/1995 | Dean et al. | 424/1.69 |
| 5,443,815 | 8/1995 | Dean et al. | 424/1.69 |
| 5,480,970 | 1/1996 | Pollak et al. | 530/328 |

FOREIGN PATENT DOCUMENTS

| | | |
|---|---|---|
| 0135160 | 3/1985 | European Pat. Off. |
| 173424 | 3/1986 | European Pat. Off. |
| 0188256 | 7/1986 | European Pat. Off. |
| 0237150 | 9/1987 | European Pat. Off. |
| 0271806 | 6/1988 | European Pat. Off. |
| 0284071 | 9/1988 | European Pat. Off. |
| 0412012 | 8/1990 | European Pat. Off. |
| 0403243 | 12/1990 | European Pat. Off. |
| 483704 | 5/1992 | European Pat. Off. |
| 515313 | 11/1992 | European Pat. Off. |
| 061819 | 5/1994 | European Pat. Off. |
| 2328453 | 10/1975 | France . |
| 2255579 | 6/1990 | United Kingdom . |
| WO8807382 | 10/1988 | WIPO . |
| WO8907456 | 8/1989 | WIPO . |
| WO8909405 | 10/1989 | WIPO . |
| WO8912625 | 12/1989 | WIPO . |
| WO9010463 | 9/1990 | WIPO . |
| 9015818 | 12/1990 | WIPO . |
| WO9015818 | 12/1990 | WIPO . |
| WO9101144 | 2/1991 | WIPO . |
| WO9213572 | 8/1992 | WIPO . |
| WO9310747 | 6/1993 | WIPO . |
| WO9312819 | 7/1993 | WIPO . |
| WO9315770 | 8/1993 | WIPO . |
| WO9317719 | 9/1993 | WIPO . |
| WO9323085 | 11/1993 | WIPO . |
| WO9400489 | 1/1994 | WIPO . |
| WO9423758 | 10/1994 | WIPO . |
| WO9426295 | 11/1994 | WIPO . |
| WO9500553 | 1/1995 | WIPO . |
| WO9503330 | 2/1995 | WIPO . |

OTHER PUBLICATIONS

Rhodes et al., *Chem. Abs.* 119(15):155015h, PCT Int. Appl. WO 93/12819, A, Jul. 8, 1993.

Rhodes, "Considerations in the Radiolabeling of Albumin," *Sem. Nucl. Med.* 4: 281–293 (1974).

Davidson et al., "A New Class of Oxotechnetium(5+) Chelate Complexes a $TcON_2S_2$ Core," *Inorg. Chem.* 20:1629–1632 (1981).

Fritzberg et al., "Synthesis and Biological Evaluation of Tc–99m N,N'–Bis(mercaptoacetyl)–2,3–diaminopropanoate: A Potential Replacement for [$^{131}$I]o–iodohippurate," *J. Nucl. Med.* 23: 592–598 (1982).

Khaw et al., "Technetium–99m Labeling of Antibodies to Cardiac Myosin Fab and to Human Fibrinogen," *J. Nucl. Med.* 23: 1011–1019 (1982).

Byrne and Tolman, "Technetium–99m Bifunctional Chelating Agent—Thiolactone for Coupling to Biomolecules, $N_2S_2$ Ligand for Chelation to Technetium," *J. Nucl. Med.* 24:P126 (1983).

Bryson et al., "Neutral Technetium(V) Complexes with Amide–Thiol–Thioether Chelating Ligands," *Inorg. Chem.* 27:2154–2161 (1988).

Bryson et al., "Protecting Groups in the Preparation of Thiolate Complexes of Technetium," *Inorg. Chem.* 29:2948–2951 (1990).

Knight et al., "Thrombus Imaging with Tc–99m Synthetic peptides Reactive with Activated Platelets," *J. Nucl. Med.* 31:757 #209 (1990).

Kwekkeboom et al., "[In–111–DTPA–D–Phe]$^1$–Octreotide Scintigraphy in Neuroendocrine Tumors," *J. Nucl. Med.* 32:981 (1991).

(List continued on next page.)

*Primary Examiner*—Gary E. Hollinden
*Assistant Examiner*—Dameron Jones
*Attorney, Agent, or Firm*—Patricia A. McDaniels; Kevin E. Noonan

[57] ABSTRACT

The invention elates to radiolabeled imaging of a mammalian body. The invention in particular provides for reagents labeled with technetium-99m for such imaging. The invention provides peptides which bind Tc-99m and which can be targeted to specific sites within a mammalian body.

6 Claims, No Drawings

OTHER PUBLICATIONS

Albert et al., "A Somatostatin Analogue to Image SS–Receptor–Positive Tumors: [In–111–DTPA–D–Phe]$^1$–Octreotide (SDZ 215–811)," *Abstract LM10*, 12$^{th}$ American Peptide Symposium (1991).

Cox et al., "Technetium Labeled Somatostatin: A Potential Agent for In Vivo Tumor Localization," Abstract, 7$^{th}$ International Symposium on Radiopharmacology, p. 16 (1991).

Lister–James et al., "A Structure–Activity–Relationship(SAR) Study of Somatostatin Receptor–Binding Peptides Radiolabeled With Tc–99m," *The Journal of Nuclear Medicine* 35(5):257P–258P, May 5, 1994.

Pritchard et al., "Indium–III–Labeled Antibody Heavy Metal Chelate Conjugates: A Potential Alternative to Radioiodination," *Proceedings of the Society for experimental Biology and Medicine* 151:297–302 (1976).

Zubay, (1983), Biochemistry, Protein Structure and Function, pp. 3–7.

Merrifield et al (1982). Biochemistry, vol. 21, pp. 5020–5031. Synthesis of the Antibacterial Peptide Cecropin A (1–33).

Houghten (1985). General Method for the Rapid Solid–Phase Snythesis of Large Numbers of Peptides: Specificity of Antigen–Antibody Interaction at the Level of Individual Amino Acids (Simultaneous Multiple–Peptide Synthesis. Proc. Natl. Acad. Sci. (USA), vol. 82, pp. 5131–5135.

TECHNETIUM-99M LABELED PEPTIDES FOR IMAGING COMPRISING A SINGLE THIOL MOIETY

This is a divisional of application Ser. No. 07/807,062, filed Nov. 27, 1991, now U.S. Pat. No. 5,443,815, issued Aug. 16, 1995.

BACKGROUND OF THE INVENTION

1. Field of the Invention

This invention relates to radiodiagnostic reagents and peptides, and methods for producing labeled radiodiagnostic agents. Specifically, the invention relates to technetium-99m (Tc-99m) labeled reagents, methods and kits for making such reagents, and methods for using such reagents. In particular, the invention relates to Tc-99m labeled peptides comprised of between 4 and 100 amino acid residues and covalently linked to a radioisotope complexing group.

2. Description of the Prior Art

The use of chelating agents for radiolabeling polypeptides is known in the prior art.

Byrne et al., U.S. Pat. No. 4,434,151 describe homocysteine thiolactone bifunctional chelating agents that can couple radionuclides to terminal amino-containing compounds capable of localizing in an organ or tissue to be imaged.

Fritzberg, U.S. Pat. No. 4,444,690 describes a series of technetium-chelating agents based on 2,3-bis (mercaptoacetamido) propanoate.

Gansow et al., U.S. Pat. No. 4,472,509 teach methods of manufacturing and purifying metal chelate-conjugated monoclonal antibodies.

Byrne et al., U.S. Pat. Nos. 4,571,430 and 4,575,556 describe novel homocysteine thiolactone bifunctional chelating agents for chelating radionuclides that can couple radionuclides to terminal amino-containing compounds capable of localizing in an organ or tissue to be imaged.

Nicolotti et al., U.S. Pat. No. 4,861,869 describe bifunctional coupling agents useful in forming conjugates with biological molecules such as antibodies. This reference describes compounds such as S-benzoylmercaptoacetylglycylglycylglycine.

European Patent Application No. 84109831.2 describes technetium chelating complexes of bisamido-bisthio-ligands and salts thereof, used primarily as renal function monitoring agents.

European Patent Application No. 86100360.6 describes dithiol, diamino, or diamidocarboxylic acids or amine complexes useful for making technetium imaging agents.

European Patent Application No. 88104755.9 describes various S-protected mercaptoacetylglycylglycine chelating groups bound to large proteins such as antibodies.

Albert et al., UK Patent Application No. 8927255.3 disclose radioimaging using somatostatin derivatives such as octreotide labeled with $^{111}$In via a chelating group bound to the amino terminus.

Flanagan et al., European Patent Application No. 90306428.5 disclose Tc-99m labeling synthetic peptide fragments via a set of organic chelating molecules.

Albert et al., European Patent Application No. WO 91/01144 disclose radioimaging using radiolabeled peptides related to growth factors, hormones, interferons and cytokines and comprised of a specific recognition peptide covalently linked to a radionuclide chelating group.

Davison et al., Inorg. Chem. 20: 1629–1632 (1981) disclose oxotechnetium chelate complexes.

Fritzberg et al., J. Nucl. Med. 23: 592–598 (1982) disclose a technetium chelating agent based on N,N'-bis (mercaptoacetyl)-2,3-diaminopropanoate.

Byrne and Tolman, J. Nucl. Med. 24: P126 (1983) disclose a bifunctional thiolactone chelating agent for coupling Tc-99m to biological molecules.

Bryson et al., Inorg. Chem. 27: 2154–2161 (1988) describe thiolate ligands for complexing with technetium.

Bryson et al., Inorg. Chem. 29: 2948–2951 (1990) describe thiolate ligands for complexing with technetium.

Kwekkeboom et al., J. Nucl. Med. 32: 981 (1991) Abstract #305 relates to radiolabeling somatostatin analogues with $^{111}$In.

Albert et al., Abstract LM10, 12th American Peptide Symposium (1991) describe uses for $^{111}$In-labeled diethylenetriaminopentaacetic acid-derivatized somatostatin analogues.

A variety of radionuclides are known to be useful for radioimaging, including $^{67}$Ga, $^{99m}$Tc (Tc-99m), $^{111}$In, $^{123}$I, $^{125}$I, $^{169}$Yb or $^{186}$Re. The sensitivity of imaging methods using radioactively-labeled peptides is much higher than other techniques known in the art, since the specific binding of the radioactive peptide concentrates the radioactive signal over the cells of interest, for example, tumor cells.

Methods for labeling peptides and polypeptides with Tc-99m have been disclosed in the prior art.

Dean, co-pending U.S. patent application Ser. No. 07/653,012 teaches reagents and methods for preparing peptides comprising a Tc-99m chelating group covalently linked to a specific binding peptide for radioimaging in vivo, and is hereby incorporated by reference.

Fritzberg, U.S. Pat. No. 4,444,690 describes a series of technetium-chelating agents based on 2,3-bis (mercaptoacetamido)propanoate.

Gansow et al., U.S. Pat. No. 4,472,509 teach methods of manufacturing and purifying Tc-99m chelate-conjugated monoclonal antibodies.

Reno and Bottino, European Patent Application No. 87300426.1 disclose radiolabeling antibodies with Tc-99m.

Bremer et al., EPC Application No. 87118142.6 disclose organ-specific radioimaging using Tc-99M radiolabeled proteins.

Pak et al., European Patent Application No. WO 88/07382 disclose a method for labeling antibodies with Tc-99m.

Goedemans et al., PCT Application No. WO 89/07456 describe radiolabeling proteins using cyclic thiol compounds, particularly on 2-iminothiolane and derivatives.

Schochat et al., PCT Application No. WO 89/09405 disclose direct radiolabeling of proteins comprised of at least one "pendent" sulfhydryl group.

Dean et al., PCT Application No. WO 89/12625 describe bifunctional coupling agents for Tc-99m labeling of proteins or peptides.

Thornback et al., EPC Application No. 90402206.8 describe preparation and use of radiolabeled proteins or peptides using thiol-containing compounds, particularly 2-iminothiolane.

Stuttle, PCT Application No. WO 90/15818 describes Tc-99m labeling of RGD-containing oligopeptides.

Rhodes, Sem. Nucl. Med. 4: 281–293 (1974) teaches the labeling of human serum albumin with Tc-99m.

Khaw et al., J. Nucl. Med. 23: 1011–1019 (1982) disclose methods for labeling biologically active macromolecules with Tc-99m.

Byrne and Tolman, supra, disclose a bifunctional thiolactone chelating agent for coupling Tc-99m to biological molecules.

Knight et al., Abstract #209, 37th Annual Meeting, Society for Nuclear Medicine (1990) describe thrombus imaging with Tc-99m labeled peptides.

Cox et al., Abstract, 7th International Symposium on Radiopharmacology, p. 16, 1991, disclose the use of $^{131}$I- and $^{111}$In-labeled somatostatin analogues in radiolocalization of endocrine tumors in vivo by scintigraphy.

SUMMARY OF THE INVENTION

The present invention provides scintigraphic imaging agents that are radioactively-labeled peptides. The peptides of the invention are comprised of between 4 and 100 amino acid residues, covalently linked to a radioisotope complexing group wherein the complexing group binds a radioisotope.

Preferred embodiments of the present invention are peptides that are covalently linked to radioisotope complexing groups comprising a thiol moiety having the following structure:

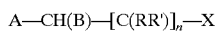

wherein A is H or HOOC; B is H, SH or NHR", where R" is H or lower alkyl; X is SH or NHR", where R" is H or lower alkyl; R and R' are independently H or lower alkyl; n is 0, 1 or 2; and: 1. where B is NHR", where R" is H or lower alkyl, X is SH and n is 1 or 2; and 2. where X is NHR", where R" is H or lower alkyl, B is SH and n is 1 or 2; 4. where B is H, A is HOOC, X is SH and n is 0 or 1; and wherein the thiol moiety is in the reduced form.

The invention encompasses peptides for labeling with Tc-99m and imaging target sites within a mammalian body comprising between 4 and 100 amino acid residues, covalently linked to a radioisotope complexing group wherein the complexing group binds a radioisotope. The invention encompasses methods for making such peptides covalently linked to a radioisotope complexing group. The invention also includes Tc-99m complexes and methods for preparation of such Tc-99m complexes and methods for using the Tc-99m complexes to image target sites within a mammalian body.

DETAILED DESCRIPTION OF THE INVENTION

The present invention provides Tc-99m labeled peptides for imaging target sites within a mammalian body that comprise between 4 and 100 amino acid residues and are covalently linked to a radioisotope complexing group wherein the complexing group binds a radioisotope.

Labeling with Tc-99m is an advantage of the present invention because the nuclear and radioactive properties of this isotope make it an ideal scintigraphic imaging agent. This isotope has a single photon energy of 140 keV and a radioactive half-life of about 6 hours, and is readily available from a $^{99}$Mo-$^{99m}$Tc generator. Other radionuclides known in the prior art have effective half-lives which are much longer (for example, $^{111}$In, which has a half-life of 67.4 h) or are toxic (for example, $^{125}$I).

Peptides of the present invention can be chemically synthesized in vitro. Peptides of the present invention can generally advantageously be prepared on an amino acid synthesizer. The peptides of this invention can be synthesized wherein the complexing group is covalently linked to the peptide during chemical in vitro synthesis, using techniques well known to those with skill in the art. Such peptides covalently-linked to the complexing group upon synthesis are advantageous because specific sites of covalent linkage can be determined therein.

In forming a complex of radioactive technetium with the peptides of this invention, the technetium complex, preferably a salt of Tc-99m pertechnetate, is reacted with the peptides of this invention in the presence of a reducing agent; in a preferred embodiment, the reducing agent is stannous chloride. In an additional preferred embodiment, the reducing agent is a solid-phase reducing agent. Complexes and means for preparing such complexes are conveniently provided in a kit form comprising a sealed vial containing a predetermined quantity of the peptides of the invention that are to be labeled and a sufficient amount of reducing agent to label the peptide with Tc-99m. Alternatively, the complex may be formed by reacting the peptides of this invention with a pre-formed labile complex of technetium and another compound known as a transfer ligand. This process is known as ligand exchange and is well known to those skilled in the art. The labile complex may be formed using such transfer ligands as tartrate, citrate, gluconate or mannitol, for example. Among the Tc-99m pertechnetate salts useful with the present invention are included the alkali metal salts such as the sodium salt, or ammonium salts or lower alkyl ammonium salts. The reaction of the peptides of this invention with Tc-pertechnetate or preformed Tc-99m labile complex can be carried out in an aqueous medium at room temperature. The anionic complex which has a charge of [−1] is formed in the aqueous medium in the form of a salt with a suitable cation such as sodium cation, ammonium cation, mono, di- or tri-lower alkyl amine cation, etc. Any conventional salt of the anionic complex with a pharmaceutically acceptable cation can be used in accordance with this invention.

In another embodiment of the present invention, the peptides of the invention that are to be labeled are reduced prior to labeling by incubating the peptides with a reducing agent. In a preferred embodiment, the reducing agent is stannous chloride. In an additional preferred embodiment, the reducing agent is a solid-phase reducing agent. The pre-reduced peptide is then labeled by reaction with a Tc-99m under reducing conditions or with pre-reduced Tc-99m or Tc-99m complex.

In a preferred embodiment of the invention, a kit for preparing technetium-labeled peptides is provided. The peptides of the invention can be chemically synthesized using methods and means well-known to those with skill in the art and described hereinbelow. Peptides thus prepared are comprised of between 4 and 100 amino acid residues, and are covalently linked to a radioisotope complexing group wherein the complexing group binds a radioisotope. An appropriate amount of the peptide is introduced into a vial containing a reducing agent, such as stannous chloride or a solid-phase reducing agent, in an amount sufficient to label the peptide with Tc-99m. An appropriate amount of a transfer ligand as described (such as tartrate, citrate, gluconate or mannitol, for example) can also be included. Technetium-labeled peptides according to the present invention can be prepared by the addition of an appropriate amount of Tc-99m or Tc-99m complex into the vials and reaction under conditions described in Example 2 hereinbelow.

Radioactively labeled peptides provided by the present invention are provided having a suitable amount of radioactivity. In forming the Tc-99m radioactive anionic complexes, it is generally preferred to form radioactive complexes in solutions containing radioactivity at concentrations of from about 0.01 millicurie (mCi) to 100 mCi per ml.

Technetium-labeled peptides provided by the present invention can be used for visualizing organs such as the kidney for diagnosing disorders in these organs, and tumors, such as gastrointestinal tumors, myelomas, small cell lung carcinoma and other APUDomas, endocrine tumors such as medullary thyroid carcinomas and pituitary tumors, brain tumors such as meningiomas and astrocytomas, and tumors of the prostate, breast, colon, and ovaries can also be imaged. In accordance with this invention, the technetium-labeled peptides or anionic complexes either as a complex or as a salt with a pharmaceutically acceptable cation are administered in a single unit injectable dose. Any of the common carriers known to those with skill in the art, such as sterile saline solution or plasma, can be utilized after radiolabeling for preparing the injectable solution to diagnostically image various organs, tumors and the like in accordance with this invention. Generally, the unit dose to be administered has a radioactivity of about 0.01 mCi to about 100 mCi, preferably 1 mCi to 20 mCi. The solution to be injected at unit dosage is from about 0.01 ml to about 10 ml. After intravenous administration, imaging of the organ or tumor in vivo can take place in a matter of a few minutes. However, imaging can take place, if desired, in hours or even longer, after injecting into patients. In most instances, a sufficient amount of the administered dose will accumulate in the area to be imaged within about 0.1 of an hour to permit the taking of scintiphotos. Any conventional method of scintigraphic imaging for diagnostic purposes can be utilized in accordance with this invention.

The technetium-labeled peptides and complexes provided by the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma.

The methods for making and labeling these compounds are more fully illustrated in the following Examples. These Examples illustrate certain aspects of the above-described method and advantageous results. These Examples are shown by way of illustration and not by way of limitation.

EXAMPLE 1

Solid Phase Peptide Synthesis

Solid phase peptide synthesis (SPPS) was carried out on a 0.25 millimole (mmole) scale using an Applied Biosystems Model 431A Peptide Synthesizer and using 9-fluorenylmethyloxycarbonyl (Fmoc) amino-terminus protection, coupling with 2-(1H-benzotriazol-1-yl)-1,1,3,3-tetramethyluronium hexafluorophosphate/hydroxybenzotriazole (HBTU/HOBT), and using p-hydroxymethylphenoxymethyl-polystyrene (HMP) resin for carboxyl-terminus acids or Rink amide resin for carboxyl-terminus amides. Resin-bound products were routinely cleaved using a solution comprised of trifluoroacetic acid, water, thioanisole, ethanedithiol, and triethylsilane, prepared in ratios of 100:5:5:2.5:2 for 1.5–3 h at room temperature. Crude peptides were purified by preparative high pressure liquid chromatography (HPLC) using a Waters Delta Pak C18 column and gradient elution using 0.1% trifluoroacetic acid (TFA) in water modified with acetonitrile. Acetonitrile was evaporated from the eluted fractions which were then lyophilized. The identity of each product was confirmed by fast atom bombardment mass spectroscopy (FABMS).

EXAMPLE 2

A General Method for Radiolabeling with Tc-99m 0.1 mg of a peptide prepared as in Example 1 was dissolved in 0.1 ml of 0.05M potassium phosphate buffer (pH 7.4). Tc-99m gluceptate was prepared by reconstituting a Glucoscan vial (E. I. DuPont de Nemours, Inc.) with 1.0 ml of Tc-99m sodium pertechnetate containing up to 200 mCi and allowed to stand for 15 minutes at room temperature. 25 ul of Tc-99m gluceptate was then added to the peptide and the reaction allowed to proceed at room temperature for 30 min and then filtered through a 0.2 $\mu$m filter.

The Tc-99m labeled peptide purity was determined by HPLC using a Vydak 218TP54 analytical column (RP-18, 5 micron, 220×4.6 mm) and eluted with the following gradient: 100% A (0.1% TFA in $H_2O$) to 100% B ($CH_3CN:H_2O$:TFA, 70:30:0.1) over 10 minutes at a flow rate of 1.2 ml/min; and then held at the 100% B solution for 5 minutes. Radioactive components were detected by an in-line radiometric detector linked to an integrating recorder. Tc-99m gluceptate and Tc-99m sodium pertechnetate elute between 1 and 4 minutes under these conditions, whereas the Tc-99m labeled peptide eluted after a much greater amount of time.

The following Table illustrates successful Tc-99m labeling of peptides prepared according to Example 1 using the method described herein.

TABLE I

| Peptides Prepared and Radiolabeled | FABMS MH+ Found/Theoretical | Radiochemical Yield | HPLC Rt (min) |
| --- | --- | --- | --- |
| YRALVDTLKFVTQAEGAKC.NH$_2$ (SEQ. ID NO: 1) | 2113/2113.1 | 92% | 11–15.5 |
| GRGDGGC (SEQ. ID NO: 2) | 769/768.3 | 98% | 13–15 |
| maGGGRGDF[a] (SEQ ID NO: 3) | 739/739.3 | 98% | 13–15 |
| PenGGGRALVDTLK.NH$_2$[b] (SEQ. ID NO: 4) | 1216.3/1216.7 | 98% | 14.8 |
| maGGGGRALVDTLK.NH$_2$ (SEQ. ID NO: 4) | 1160/1160.5 | 97% | 14.3 |
| mmpGGGRALVDTLK.NH$_2$[c] (SEQ. ID NO: 4) | 1187.4/1186.7 | 98% | 14.9–15.5 |

[a]ma = mercaptoacetic acid
[b]Pen = L-penicillamine
[c]mmp = 2-mercapto-2-methylpropionic acid It should be understood that the foregoing disclosure emphasizes certain specific embodiments of the invention and that all modifications or alternatives equivalent thereto are within the spirit and scope of the invention as set forth in the appended claims.

What is claimed is:

1. A compound comprising:
   a) a peptide having between 4 and 100 amino acid residues; and
   b) covalently linked to the peptide, a radioisotope complexing group comprising a single reduced thiol moiety that is:

$$A-CH(B)-[C(RR')]_n-X$$

wherein
   A is H or HOOC;
   B is H, SH, or NHR", where R" is H or lower alkyl;
   X is SH or NHR", where R" is H or lower alkyl;
   R and R' are independently H or lower alkyl;
   n is 0, 1 or 2; and
   where B is NHR", X is SH and n is 1 or 2;
   where X is NHR", B is SH and n is 1 or 2;

where B is H, A is HOOC, X is SH and n is 0 or 1;

wherein the compound is capable of imaging target sites within a mammalian body when labeled with technetium-99m.

2. The compound according to claim 1 wherein the peptide and the complexing group are covalently linked through one or more amino acids.

3. The compound according to claim 1 wherein the peptide is chemically synthesized in vitro.

4. The compound according to claim 3 wherein the peptide is synthesized by solid phase peptide synthesis.

5. The compound according to claim 3 wherein the complexing group is covalently linked to the peptide during in vitro chemical synthesis.

6. The compound according to claim 4 wherein the completing group is covalently linked to the peptide during solid phase peptide synthesis.

* * * * *

UNITED STATES PATENT AND TRADEMARK OFFICE
CERTIFICATE OF CORRECTION

PATENT NO. : 5,807,537
DATED : September 15, 1998
INVENTOR(S) : Dean; McBride; Buttram It is certified that error appears in the above-identified patent and that said Letters Patent is hereby corrected as shown below:

On the title page in the ABSTRACT [57] please replace "elates" with -relates-.
At column 10, line 7 please replace "completing" with -complexing-.

Signed and Sealed this

Ninth Day of February, 1999

Attest:

Attesting Officer

Acting Commissioner of Patents and Trademarks

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 19 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:1:

```
Tyr Arg Ala Leu Val Asp Thr Leu Lys Phe Val Thr Gln Ala Glu Gly
1               5                   10                  15
Ala Lys Cys
```

( 2 ) INFORMATION FOR SEQ ID NO:2:

( i ) SEQUENCE CHARACTERISTICS:
      ( A ) LENGTH: 7 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:2:

```
Gly Arg Gly Asp Gly Gly Cys
1               5
```

( 2 ) INFORMATION FOR SEQ ID NO:3:

( i ) SEQUENCE CHARACTERISTICS:
      ( A ) LENGTH: 7 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:3:

```
Gly Gly Gly Arg Gly Asp Phe
1               5
```

( 2 ) INFORMATION FOR SEQ ID NO:4:

( i ) SEQUENCE CHARACTERISTICS:
      ( A ) LENGTH: 11 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:4:

```
Gly Gly Gly Arg Ala Leu Val Asp Thr Leu Lys
1               5                   10
```